United States Patent
Kalbasenka et al.

(10) Patent No.: US 10,920,250 B2
(45) Date of Patent: Feb. 16, 2021

(54) MAGNESIUM LACTATE FERMENTATION PROCESS

(71) Applicant: PURAC BIOCHEM BV, Gorinchem (NL)

(72) Inventors: Aliaksei Kalbasenka, Gorinchem (NL); Jeroen Bokhove, Gorinchem (NL)

(73) Assignee: PURAC BIOCHEM BV, Gorinchem (NL)

(*) Notice: Subject to any disclaimer, the term of this patent is extended or adjusted under 35 U.S.C. 154(b) by 0 days.

(21) Appl. No.: 16/092,378

(22) PCT Filed: Apr. 10, 2017

(86) PCT No.: PCT/EP2017/058547
§ 371 (c)(1),
(2) Date: Oct. 9, 2018

(87) PCT Pub. No.: WO2017/178426
PCT Pub. Date: Oct. 19, 2017

(65) Prior Publication Data
US 2019/0024125 A1 Jan. 24, 2019

(30) Foreign Application Priority Data
Apr. 12, 2016 (EP) .................... 16164820

(51) Int. Cl.
*C12P 7/56* (2006.01)
*C07C 51/02* (2006.01)
*C12M 1/36* (2006.01)

(52) U.S. Cl.
CPC ............. *C12P 7/56* (2013.01); *C07C 51/02* (2013.01); *C12M 1/36* (2013.01)

(58) Field of Classification Search
CPC combination set(s) only.
See application file for complete search history.

(56) References Cited

U.S. PATENT DOCUMENTS

2010/0323416 A1 12/2010 Guettler et al.

FOREIGN PATENT DOCUMENTS

| CN | 105018538 A | 11/2015 |
|---|---|---|
| EP | 2 604 696 A1 | 6/2013 |
| NL | 288829 A | 3/1965 |
| WO | 2013/160352 A1 | 10/2013 |
| WO | 2016/016233 A1 | 2/2016 |
| WO | 2016/016234 A1 | 2/2016 |

OTHER PUBLICATIONS

Wang, Y. et al., Bioresource Techol. 2015 vol. 198, pp. 658-663.*
Wang et al., "Efficient magnesium lactate production with in situ product removal by crystallization," Bioresource Technology, 2015, vol. 198, pp. 658-663.
Jun. 26, 2017 International Search Report issued in International Patent Application No. PCT/EP2017/058547.
Jun. 26, 2017 Written Opinion of the International Searching Authority issued in International Patent Application No. PCT/EP2017/058547.
Nov. 11, 2019 Office Action issued in Japanese Patent Application No. 2018-552689.

* cited by examiner

Primary Examiner — Heidi Reese
(74) Attorney, Agent, or Firm — Oliff PLC

(57) ABSTRACT

A fermentation process for producing magnesium lactate from a carbon source including the steps of: providing a fermentation medium including a fermentable carbon source in a fermentation reactor; fermenting the fermentation medium by a lactic acid producing microorganism in the presence of an alkaline magnesium salt to provide a fermentation broth including magnesium lactate; and recovering solid magnesium lactate from the magnesium lactate containing fermentation broth, wherein during at least 40% of the operating time of the fermentation process, the concentration of solid magnesium lactate in the fermentation broth is maintained in the range of 5-40 vol. %, calculated as solid magnesium lactate crystals on the total of the fermentation broth. The process allows stable operation at high productivity, in combination with efficient product separation.

15 Claims, No Drawings

MAGNESIUM LACTATE FERMENTATION PROCESS

The present invention relates to the production of magnesium lactate via fermentation.

Magnesium lactate has many applications, one of which is a source material for lactic acid. Lactic acid may be used in numerous applications such as the preservation of food and the preparation of biodegradable polymers. In some of these applications the quality of the starting lactic acid is of utmost importance. For instance, in the production of lactide and polylactic acid it is desirable to start with a lactic acid with high stereochemical purity. Further, the presence of impurities in the starting lactic acid may result in undesirable racemisation of lactic acid moieties leading to a lactide and a polylactic acid product of lower quality.

The increasing demand for high quality products together with the need to achieve production costs compatible with the commodities market, make it essential to be able to reduce the costs of the starting materials for the production of lactic acid while at the same time not compromising the quality.

Lactic acid is often manufactured via fermentation of carbohydrates by microorganisms. To keep the pH of the reaction medium at a value where microorganism grows well, an alkaline salt is often added during fermentation, to compensate for the decrease in pH caused by the formation of lactic acid. This results in the formation of a lactate salt. Where an alkaline magnesium salt is used, e.g., a (hydr)oxide or carbonate of magnesium, magnesium lactate will be formed. Fermentation processes wherein magnesium lactate is formed, also indicated as magnesium lactate fermentations, are known in the art.

For example, NL288829 describes a continuous fermentation process for manufacturing lactic acid where a magnesium salt or zinc salt is added during fermentation, to cause the formation of insoluble magnesium lactate or zinc lactate, which is removed from the fermentation medium.

US2010/0323416 also describes a fermentation process to form a carboxylic acid, with addition of a magnesium salt.

WO2013160352 describes a fermentation process for the manufacture of, among many other products, magnesium lactate. The process encompasses a solid product removal step comprising a hydrocyclone and a solid/liquid separation step.

Yong Wang et al., Efficient magnesium lactate production with in situ product removal by crystallization, BioResource Technology, Vol. 198, 26Sep. 2015, pp. 658-663,describes a magnesium lactate fermentation wherein magnesium lactate is removed during the fermentation. It is indicated that removal of solid product during the fermentation should be carried out at a magnesium lactate concentration of 140 g/l. A magnesium lactate concentration of 140 g/1 corresponds to a crystal concentration of 5 vol. % at 42° C. In FIG. 3 of this document the product concentration in the fermentation is kept between 70 and 150 g/l during the fermentation (with a startup period of 25 hours before a value of 70 g/l is attained). As crystal formation starts at a concentration of 110 g/l, this means that for a substantial part of the fermentation there are no solid crystals present at all and otherwise only at low concentrations.

To achieve the goal of a source for lactic acid which allows reduction of costs without compromising on product quality there is need in the art for a magnesium lactate fermentation process which allows stable operation at high productivity, in combination with efficient product separation. The present invention provides such a process.

The present invention pertains to a fermentation process for producing magnesium lactate from a carbon source comprising the steps of
  providing a fermentation medium comprising a fermentable carbon source in a fermentation reactor,
  fermenting the fermentation medium by means of a lactic acid producing microorganism in the presence of an alkaline magnesium salt to provide a fermentation broth comprising magnesium lactate, and
  recovering solid magnesium lactate from the magnesium lactate containing fermentation broth,
wherein during at least 40% of the operating time of the fermentation process, the concentration of solid magnesium lactate in the fermentation broth is maintained in the range of 5-40 vol. %, calculated as solid magnesium lactate crystals on the total of the fermentation broth.

It has been found that by ensuring that the concentration of solid magnesium lactate in the fermentation broth is maintained in the range of 5-40 vol. % during at least 40% of the operating time, a process is obtained which combines a high yield with efficient product separation properties. Efficient product separation properties translate into good process stability, but also into high product quality, since it allows a good separation of the magnesium lactate from contaminants.

More specifically, it has been found that when the concentration of solid magnesium lactate is too high during a substantial part of the process, the productivity of the process decreases. Not wishing to be bound by theory it is believed that this may be caused by the presence of the magnesium lactate fermentation product somehow influencing the fermentation process, e.g., by influencing the water activity in the system, and/or by somehow influencing the microorganism. This is in contrast with conventional wisdom, which teaches that solid fermentation products do not influence fermentation.

On the other hand it has been found that if the magnesium lactate concentration is too low during a substantial part of the process, the separation of solid magnesium lactate from the fermentation broth is more difficult.

It may be preferred for the concentration of solid magnesium lactate in the fermentation broth to be at least 10 vol. %, because it has been found that a higher concentration of solid magnesium lactate results in a product with improved properties, including improved filtration properties, which makes the product easier to wash. It may be preferred for the concentration of solid magnesium lactate in the fermentation broth to be in the range of 10-35 vol. % during the stipulated part of the operating time, in particular in the range of 10-30 vol. %, in some embodiments in the range of 10-25 vol. %. It may be more preferred for the solid magnesium lactate in the fermentation broth to be in the range of 15-40 vol. %, in particular 15-35 vol. %, during the stipulated part of the operating time, more in particular in the range of 15-30 vol. %, in some embodiments in the range of 15-25 vol. %. In some embodiments it may be preferred for the concentration of solid magnesium lactate in the fermentation broth to be in the range of 20-40 vol. %, in particular 20-35 vol. % during the stipulated part of the operating time, more in particular in the range of 20-30 vol. %, in some embodiments in the range of 20-25 vol. %.

The concentration of solid magnesium lactate in the fermentation broth is determined in accordance with the following procedure: A 1 ml homogeneous sample is taken from the fermentation broth using an Eppendorf tube. The sample is centrifuged for 2 minutes at 1300 rpm. The volume percentage of the solid layer is determined visually.

This solid layer comprises both solid magnesium lactate and biomass. To compensate for the amount of biomass, the amount of biomass may be determined separately by methods known in the art, e.g., by determining the optical density at 600 nm of a fermentation broth sample from which crystals have been removed by diluting it to 5 vol. % in a solution of 0.5 N EDTA adjusted to pH 8 with KOH, and comparing it with the OD600 nm of standard biomass solutions.

The volume percentage of solid magnesium lactate can then be determined by subtracting the volume percentage of biomass from the percentage obtained in the centrifuge procedure described above.

The starting point for the operating time of the fermentation process is the point in time when all medium components have been provided to the reactor, the fermentation medium has been brought to fermentation conditions, such as the selected pH and temperature, and the microorganism has been provided to the reactor. At that point in time all conditions have been met for the fermentation to begin.

The end point for the operating time of the fermentation process is the point in time when product formation has essentially stopped, i.e., when the production in g/l.h. is below 10% of the maximum value of production in g/l.h during the process. This will generally be when the carbon source has been depleted.

The total operating time of the process according to the invention may vary within wide ranges. For commercial operation a suitable minimum operating time is 10 hours. If the operating time is below this value, the period of time (in hours) during which the concentration of magnesium lactate is within the stipulated range will be so short that meaningful commercial operation may be difficult to achieve. It may be preferred for the total operating time of the process according to the invention to be at least 24 hours, in particular at least 48 hours. The maximum number of hours is not critical. As described elsewhere herein, for a continuous process the total operating time may in principle be indefinite. A value of 2 years may be mentioned as a general maximum.

The concentration of solid magnesium lactate in the fermentation broth will generally not be in the stipulated vol. % range during the entire operating time. For example, at the beginning of the fermentation, it may be that there is no magnesium lactate present in the medium. Upon start-up of the fermentation, magnesium lactate is formed, which will first be in the dissolved state. Upon the formation of more magnesium lactate, the fermentation medium will become saturated with magnesium lactate, and solid magnesium lactate crystals will begin to form. It will then take some time for the value of 10 vol. % to be reached.

On the other hand, near the end of the fermentation, when the provision of carbon source is stopped, it can be desirable to let the fermentation run without further product removal, which may result in the concentration of solid magnesium lactate in the fermentation broth to become higher than 40 vol. %. Further, especially when product removal is intermittent, it may be that the concentration of solid magnesium lactate reaches a value of above 40 vol. % during the process at some points in time.

The percentage of the operating time during which the concentration of solid magnesium lactate is maintained in the ranges specified above, is therefore dependent on the amount of time taken up by the startup phase and the end phase described above, in relationship to the time period between such startup and end phase. Therefore, the longer the operating time is, the higher the percentage of operating time can be during which the concentration of solid magnesium lactate is in the stipulated range.

It is preferred that during at least 60% of the operating time of the fermentation process, the concentration of solid magnesium lactate in the fermentation broth is maintained in the stipulated range, preferably during at least 70% of the operating time, more preferably during at least 80% of the operating time, in some cases during at least 90% of the operating time.

The process according to the invention may be a batch process, a fed-batch process, or a continuous process.

In one embodiment, the fermentation process according to the invention is a batch process. Within the present specification a batch process is defined as a process wherein the carbon source is provided to the fermentation reactor at the beginning of the reaction, and no (substantial portions of) carbon source are provided during the process.

In one embodiment, the fermentation process according to the invention is a fed-batch process. Within the present specification a fed-batch process is a process wherein at least the carbon source is provided to the fermentation reactor at the beginning of the reaction and during the reaction, which process has a predetermined end point beyond which fermentation cannot be continued due to, e.g., the built-up of impurities.

In one embodiment, the fermentation process according to the invention is a continuous fermentation process. Within the context of the present specification a continuous fermentation process is a process wherein at least the carbon source is provided to the fermentation reactor at the beginning of the reaction and during the reaction, wherein the process does not have a predetermined end point. In general, the total volume of the fermentation medium is kept more or less constant. This means that, in view of the addition of carbon source during the fermentation which results in an increase in the volume of the fermentation medium, content will be removed during the fermentation, in this case in the form of solid magnesium lactate, optionally in combination with some liquid fermentation medium. In principle, a continuous fermentation can run indefinitely, although it will at some point in time be discontinued for unit maintenance. The concepts of batch fermentation, fed-batch fermentation, and continuous fermentation are known to the skilled person.

Conventionally in batch fermentations and fed-batch fermentations, the fermentation is continued until the carbon source has been depleted to such an extent that fermentation stops. The concentration of magnesium lactate in the fermentation broth is determined by the amount of carbon source, and can increase to very high values, e.g., of the order of 50 vol. %, calculated on the total of the fermentation broth. These very high concentrations can be obtained because magnesium lactate is present in solid form.

In the present invention, however, the process will be carried out in such a manner by appropriate recovery of solid magnesium lactate from the fermentation broth that the concentration of solid magnesium lactate is kept in the stipulated ranges during the specified part of the operating time.

In one embodiment of the present invention, the fermentation process is a continuous fermentation process. In a continuous fermentation process carbon source and other compounds are added during the fermentation process, so that the process can in principle run indefinitely. In continuous fermentation processes, intermittent product removal will take place, to ensure sufficient space in the reaction vessel for the fermentation to continue. In the magnesium lactate fermentations described in literature, e.g., in NL288829, no information is provided on the magnesium lactate concentration in the fermentation broth at which product removal is carried out. In contrast, in the present invention it has been found that, contrary to expectations, by keeping the solid magnesium lactate concentration within a specified range during a specified part of the operating time a fermentation process is obtained which combines a product which shows good separation properties with a high volumetric productivity. The use of continuous fermentation is a preferred embodiment of the present invention, especially where the concentration of solid magnesium lactate is kept in the stipulated range during at least 70% of the operating time, more preferably during at least 80% of the operating time, still more preferably during at least 90% of the operating time.

The concentration of solid magnesium lactate in the fermentation broth is regulated be recovering solid magnesium lactate therefrom.

Recovery of solid magnesium lactate will generally be carried out during the process. It can be done in manners known in the art, e.g., by the steps of withdrawing fermentation broth comprising solid magnesium lactate from the fermentation reactor, and removing solid magnesium lactate from the fermentation broth. The removal of solid magnesium lactate from the fermentation broth can be done by methods known in the art, e.g., via filtration, centrifugation, decantation, or combinations thereof.

In one embodiment the fermentation broth from which solid magnesium lactate has been removed is recycled in part or in its entirety to the fermentation reactor. This may be attractive to restore biomass from the fermentation broth to the fermentation reactor.

The removal of magnesium lactate can be carried out in discrete steps in an intermittent fashion, but also in a continuous manner. Continuous magnesium lactate removal is considered preferred, because it allows accurate control of the amount of magnesium lactate present in the fermentation broth. It can also efficiently be integrated in a continuous fermentation process, which is a preferred embodiment of the present invention.

In general, if a step is carried out in which fermentation broth comprising solid magnesium lactate is withdrawn from the reactor, the volume of fermentation broth withdrawn in an individual step is at most 40 vol. % of the fermentation medium present in the reactor. Higher percentages will make it difficult to maintain the concentration of solid magnesium lactate within the specified range. It may be preferred if the volume of fermentation broth withdrawn in an individual step is at most 30 vol. % of the fermentation medium present in the reactor, in particular at most 20 vol. %, more in particular at most 10 vol. %.

The process according to the invention also encompasses the steps of providing a fermentation medium comprising a fermentable carbon source in a fermentation reactor, and fermenting the fermentation medium by means of a lactic acid producing microorganism in the presence of an alkaline magnesium salt to provide a fermentation broth comprising magnesium lactate. These steps are generally known to the person skilled in the art. They will be elucidated below for background purposes.

In the process according to the invention a fermentation medium comprising a fermentable carbon source is provided in a fermentation reactor. The term "fermentable carbon source" as used herein refers to carbohydrates which can be fermented by a lactic acid producing microorganism. Examples of fermentable carbon sources are C5 sugars, C6 sugars, oligomers thereof (e.g. dimeric C12 sugars) and/or polymers thereof, but also compounds like glycerol. By C5 sugars and C6 sugars is meant saccharides with 5 and 6 carbon atoms, respectively, and by C12 sugars it is meant saccharides with 12 carbon atoms (e.g. a disaccharide). The type of fermentable carbon source that a specific microorganism is able to ferment may vary and typically depends on the lactic acid-producing microorganism used. Examples of common sugars fermentable by lactic acid producing microorganisms may include C5 sugars such as arabinose, xylose and ribose; C6 sugars such as glucose, fructose, galactose, rhamnose and mannose; and C12 sugars such as sucrose, maltose and isomaltose. It is within the scope of the skilled person to select a suitable combination of carbon source and microorganism based on his common general knowledge.

The concentration of the carbon source in the reaction medium will depend on the nature of the carbon source, the nature of the microorganism, and the further fermentation conditions. It is within the scope of the skilled person to select a suitable concentration here.

The fermentation medium may be provided by combining additional nutrients with the carbon source and water. The additional nutrients may be added in any order and in solid form, as solutions or as suspensions (e.g. in water).

Suitable nutrients for use in fermentation to manufacture lactic acid or lactate salts are known in the art. The additional nutrients may be selected from at least one of, for instance, mineral salts (e.g. a source of mineral nitrogen, phosphate, sulfur and trace elements such as zinc, magnesium, calcium, manganese, potassium, sodium, boric, iron, cobalt, copper, molybdenum, nickel, aluminum etc.) and a source of organic nitrogen (e.g. yeast autolysates and hydrolysates, plant protein hydrolysates, animal protein hydrolysates, and soluble by-products from steeping wheat or maize). Such organic nitrogen sources generally provide nitrogen in the form of, e.g., free amino acids, oligopeptides, peptides, vitamins and traces of enzyme cofactors. Such organic nitrogen sources further may also be added individually and/or in pure form.

The pH of the fermentation medium may be adjusted to a pH suitable for fermentation with the microorganism of choice, prior to inoculation. Generally, the pH may be adjusted to a pH from about 2.0 to about 8.0, in particular from about 4.0 to about 7.5. Depending on the initial pH of the fermentation medium, adjusting the pH may be performed by addition of a base (e.g. an alkaline magnesium salt) or an acid (e.g. $H_2SO_4$) The fermentation medium is fermented by means of a lactic acid producing microorganism in the presence of an alkaline magnesium salt to provide a fermentation broth containing magnesium lactate. The fermentation is generally performed by incubating the fermentation medium with the microorganism at a suitable temperature for a suitable period of time.

During fermentation, magnesium lactate will precipitate in solid form. Whether or not precipitation of magnesium lactate occurs will depend on the concentration of fermentable carbohydrates in the fermentation medium, the fermentation temperature, the concentration of other constituents of the fermentation medium, the magnesium lactate concentration and the dilution factor of the added alkaline magnesium salt.

Suitable lactic acid producing microorganisms are known in the art and may include bacteria, fungi and yeasts, and may be selected from microorganisms that are (a) homolactic lactic acid producers or (b) heterofermentative microorganisms which produce lactic acid. The microorganisms may be genetically engineered to produce or overproduce lactic acid. Examples of such microorganisms include, but are not limited to, bacterial species of the genera *Lactobacillus, Leuconostoc, Pediococcus, Lactococcus, Streptococcus, Aerococcus, Carnobacterium, Enterococcus, Oenococcus, Sporolactobacillus, Tetragenococcus, Vagococcus, Weissella, Bacillus* (including *Bacillus coagulans, Bacillus licheniformis, Bacillus smithii, Bacillus thermolactis* and *Bacillus thermoamylovorans*), *Geobacillus* (including *Geobacillus stearothermophilus* and *Geobacillus thermoglucosidans*), *Caldicellulosiruptor* (including *Caldicellulosiruptor saccharolyticus*), *Clostridium* (including *Clostridium thermocellum*), *Thermoanaerobacterium* (including *Thermoanaerobacterium saccharolyticum*), *Thermoanaerobacter* and *Escherichia* (including *Escherichia coli*), and fungal and yeast species from the genera *Saccharomyces* (including *Saccharomyes cerevisiae*), *Kluyveromyces* (including *Kluyveromyces lactis* and *Kluyveromyces marxianus*), *Issatchenkia* (including *Issatchenkia orientalis*), *Pichia* (including *Pichia stipitis*), *Candida* (including *Candida boidinii, Candida magnolia, Candida methanosorbosa, Candida sonorensis* and *Candida utilis*) and *Rhizopus* (including *Rhizopus arrhizus, Rhizopus microspores* and *Rhizopus oryzae*). Bacterial genera that are of particular interest are *Lactobacillus, Bacillus* (including *Bacillus coagulans, Bacillus licheniformis, Bacillus smithii, Bacillus thermolactis* and *Bacillus thermoamylovorans*), *Geobacillus* (including *Geobacillus stearothermophilus* and *Geobacillus thermoglucosidans*) and *Escherichia* (including *Escherichia coli*).

Additionally or alternatively, preferred bacterial species are those that display optimal growth at a pH in the range of about 6 to about 8.

The incubation temperature may depend on the microorganism used. For example, the optimum temperature to be used may be established by analyzing the activity of the fermentation microorganism under different temperature conditions.

Generally, the temperature may be within the range from about 20 to about 80° C., in particular within the range from about 25 to about 70° C., and more in particular within the range from about 30 to about 60° C.

The alkaline magnesium salt added to the fermentation medium is used to neutralize the lactic acid excreted by the microorganisms during fermentation generating a magnesium lactate salt. A drop in pH below a critical value, depending on the microorganism used in the process, could damage the metabolic process of the microorganism and bring the fermentation process to a stop. The pH is generally adjusted during fermentation to be from about 2.0 to about 8.0, in particular from about 4.0 to about 7.5. Adjusting the pH may be performed by controlling the pH of the fermentation medium and by addition of appropriate amounts of base when necessary. The alkaline magnesium salt may be selected from, for instance, at least one of MgO, Mg(OH)2, MgCO3 and Mg(HCO3)2.

The alkaline magnesium salt may contain minor amounts of other cations.

The magnesium lactate obtained by the process according to the invention may be processed as desired. It can be subjected to intermediate purification steps in manners known in the art, e.g., via recrystallisation, resulting in purified magnesium lactate.

The magnesium lactate can, e.g., by converted to lactic acid. This can be done by various methods, including an ion exchange method, e.g. by use of an ion exchange column or electrodialysis, or acidification using a strong inorganic acid (e.g. sulfuric acid, HCl or HNO3) to provide a mixture of lactic acid and a magnesium salt in an aqueous medium. This mixture can subsequently be subjected to a lactic acid/magnesium salt separation step, resulting in the formation of lactic acid and a separate magnesium salt.

The separation step can be carried out by methods known in the art. Where the magnesium salt is in solid form, e.g., where sulphuric acid is used in the acidification step, the lactic acid/magnesium salt separation step can be in the form of a solid/liquid separation step, in which the solid magnesium salt is removed, resulting in the formation of an aqueous lactic acid solution.

Where the magnesium salt is present in the mixture as a dissolved salt, e.g., in the case of magnesium chloride where HCl was used in the acidification step, the separation of lactic acid from the magnesium salt solution can, e.g., be carried out by extracting the lactic acid from the salt solution using an organic extractant which is not miscible with the aqueous salt solution. The lactic acid can then be recovered from the extractant by, e.g., removing the solvent through evaporation, or by extracting the lactic acid from the extractant with water, resulting in the formation of an aqueous lactic acid solution.

Aqueous lactic acid solutions can be purified by methods known in the art, e.g., by treatment with active carbon. They can be concentrated by removal of water. The lactic acid can be purified, e.g., by distillation, resulting in a purified lactic acid. The lactic acid can be crystallised, if so desired, to form a solid crystalline lactic acid. It can also be subjected to an oligomerisation step by removal of water, to form lactic acid oligomers.

The lactic acid obtained by the method according to the invention can be converted to lactide. The lactide, or the lactic acid itself, can be converted to polylactic acid.

The various methods for treating the magnesium lactate, converting it to lactic acid, further treatment of lactic acid, and manufacture of lactide and polylactic acid are conventional are require no further elucidation.

The present invention is further illustrated by the following examples, without being limited thereto or thereby.

EXAMPLE 1

A magnesium lactate fermentation according to the invention was carried out as follows. Sucrose as carbon source was brought into a fermentation reactor, together with additional nutrients and water, to form a fermentation medium. The fermentation medium was brought to fermentation conditions, including a set pH and temperature. The medium was inoculated with a microorganism capable of manufacturing lactic acid. During the fermentation, the pH of the fermentation medium was monitored, and kept at the selected value by the addition of a magnesium hydroxide slurry. Sucrose as substrate was continuously added to the fermentation medium.

Periodic removal of solid magnesium lactate was carried out in such a manner that the solid magnesium lactate concentration was in the range of 10-40 vol. % for the entirety of the process, and in the range of 15-30 vol. % for about 50% of the operating time. This was effected by removing crystal slurry from the bottom of the reactor every 4-10 hours, removing solid magnesium lactate therefrom, and recycling the liquid effluent to the reactor.

It appeared that using the process according to the invention over a period of 50 hours (10 product removals) beginning at the start of the fermentation resulted in high average productivity expressed as gram magnesium lactate per liter per hour.

The magnesium lactate obtained in the process according to the invention was separated from the crystal slurry by filtration. The resulting filter cake had a moisture content of between 26 and 32 wt. %. This indicates that the filtration properties of the magnesium lactate are such that efficient product separation is possible. When the solid magnesium lactate concentration is below 5 vol. % for too long, a filter cake with a much higher moisture content will be obtained, which makes for more difficult product separation.

The invention claimed is:

1. Fermentation process for producing magnesium lactate from a carbon source comprising
   providing a fermentation medium comprising a fermentable carbon source in a fermentation reactor,
   fermenting the fermentation medium by means of a lactic acid producing microorganism in the presence of an alkaline magnesium salt to provide a fermentation broth in the fermentation reactor comprising magnesium lactate, and
   recovering solid magnesium lactate from the fermentation broth,
   wherein during at least 40% of a total operating time of the fermentation process, the recovering of solid magnesium lactate from the fermentation broth is such that an amount of solid magnesium lactate in the fermentation broth in the fermentation reactor is maintained in a range of 10 to 40 vol. %, calculated as solid magnesium lactate in a total of the fermentation broth in the fermentation reactor.

2. Process according to claim 1, wherein the amount of solid magnesium lactate in the fermentation broth in the fermentation reactor is in a range of 10 to 35 vol. % during the at least 40% of the total operating time.

3. Process according to claim 1, wherein the amount of solid magnesium lactate in the fermentation broth in the fermentation reactor is in a range of 15 to 40 vol. % during the at least 40% of the total operating time.

4. Process according to claim 1, wherein the amount of solid magnesium lactate in the fermentation broth in the fermentation reactor is in the range of 20 to 40 vol. % during the at least 40% of the total operating time.

5. Process according to claim 1, wherein during at least 60% of the total operating time of the fermentation process, the amount of solid magnesium lactate in the fermentation broth in the fermentation reactor is maintained in the range of 10 to 40 vol. %.

6. Process according to claim 1, wherein the process is a batch process, a fed-batch process, or a continuous process.

7. Process according to claim 6, wherein the process is a continuous process where the amount of solid magnesium lactate in the fermentation broth in the fermentation reactor is kept in the range of 10 to 40 vol. % during at least 70% of the total operating time.

8. Process according to claim 1, wherein the recovering solid magnesium lactate from the fermentation broth comprises withdrawing fermentation broth comprising solid magnesium lactate from the fermentation reactor, and removing solid magnesium lactate from the withdrawn fermentation broth.

9. Process according to claim 8, wherein the withdrawn fermentation broth from which solid magnesium lactate has been removed is recycled back into the fermentation reactor.

10. Process according to claim 1, wherein the recovering solid magnesium lactate from the fermentation broth is carried out in discrete steps in an intermittent fashion.

11. Process according to claim 1, wherein the recovering solid magnesium lactate from the fermentation broth is carried out in a continuous manner.

12. Process according to claim 1, wherein the fermentation process is a continuous fermentation process, and wherein the recovering solid magnesium lactate from the fermentation broth is carried out in a continuous manner.

13. Process according to claim 1, wherein the magnesium lactate is subjected to a purification step resulting in a purified magnesium lactate.

14. Process according to claim 1, wherein the magnesium lactate is converted to lactic acid by acidification, the acidification being followed by a separation step to separate the lactic acid from a magnesium salt formed during the acidification step.

15. Process according to claim 14, wherein the separated lactic acid is subjected to one or more of
    a purification step resulting in the formation of purified lactic acid,
    a crystallisation step resulting in the formation of lactic acid as a solid crystalline material,
    an oligomerisation step resulting in the formation of lactic acid oligomers, or
    a conversion process in which the separated lactic acid is converted to lactide, or to polylactic acid either directly or via lactide.

* * * * *